US009498626B2

(12) United States Patent
Frühauf et al.

(10) Patent No.: US 9,498,626 B2
(45) Date of Patent: *Nov. 22, 2016

(54) AUTOMATIC SELECTION OF REDUCTION OR ENHANCEMENT OF TRANSIENT SOUNDS

(71) Applicant: MED-EL Elektromedizinische Geraete GmbH, Innsbruck (AT)

(72) Inventors: Florian Frühauf, Rinn (AT); Ernst Aschbacher, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 50 days.

This patent is subject to a terminal disclaimer.

(21) Appl. No.: 14/564,818

(22) Filed: Dec. 9, 2014

(65) Prior Publication Data

US 2015/0163604 A1  Jun. 11, 2015

Related U.S. Application Data

(60) Provisional application No. 61/914,653, filed on Dec. 11, 2013.

(51) Int. Cl.
*A61N 1/36* (2006.01)

(52) U.S. Cl.
CPC ......... *A61N 1/3606* (2013.01); *A61N 1/36032* (2013.01); *H04R 2225/67* (2013.01)

(58) Field of Classification Search
CPC .......... H04R 25/606; H04R 2225/023; A61N 1/36032; A61N 1/36036; A61N 1/0541; G10L 21/0208; G10L 2021/02087
See application file for complete search history.

(56) References Cited

U.S. PATENT DOCUMENTS

| | | | |
|---|---|---|---|
| 6,348,070 B1 | 2/2002 | Teissl et al. | 623/11.11 |
| 6,594,525 B1 | 7/2003 | Zierhofer | 607/57 |

(Continued)

FOREIGN PATENT DOCUMENTS

| | | | |
|---|---|---|---|
| DE | 102005043314 B4 | 8/2009 | H04R 25/00 |
| EP | 1371263 B1 | 12/2010 | H04R 25/00 |
| WO | WO 99/53615 A2 | 10/1999 | H03H 21/00 |

OTHER PUBLICATIONS

Boll, *Suppression of Acoustic Noise in Speech Using Spectral Subtraction*, IEEE Trans. Acoustics, Speech, and Sig. Proc., vol. ASSP-27, No. 2, pp. 113-120, Apr. 1979.

(Continued)

*Primary Examiner* — Catherine Voorhees
(74) *Attorney, Agent, or Firm* — Sunstein Kann Murphy & Timbers LLP

(57) ABSTRACT

A system and method of generating electrode stimulation signals for electrode contacts in an electrode array associated with a hearing implant is presented. An input audio signal is processed to generate a plurality of band pass channel signals each representing an associated band of audio frequencies. A stationary noise reduction is applied so as to provide a stationary noise reduced channel envelope from each channel signal. A transient in one or more of the channel envelopes is detected. The channel envelopes are modified as a function of whether the transient is transient noise or transient speech, so as to form transient modified envelope. The transient modified envelopes are used to generate electrode stimulation signals to the electrode contacts.

20 Claims, 10 Drawing Sheets
(3 of 10 Drawing Sheet(s) Filed in Color)

(56) References Cited

U.S. PATENT DOCUMENTS

| | | | |
|---|---|---|---|
| 7,149,583 B1 | 12/2006 | Litvak | 607/57 |
| 7,219,065 B1 | 5/2007 | Vandali et al. | 704/278 |
| 7,353,169 B1 | 4/2008 | Goodwin et al. | 704/244 |
| 7,725,315 B2 | 5/2010 | Hetherington et al. | 704/233 |
| 7,869,994 B2 | 1/2011 | Nongpiur et al. | 704/266 |
| 7,953,490 B1* | 5/2011 | Fridman | A61N 1/0541 607/55 |
| 8,019,429 B2 | 9/2011 | Aschbacher et al. | 607/56 |
| 8,929,994 B2* | 1/2015 | Fruhauf | A61N 1/36032 607/57 |
| 9,126,041 B2* | 9/2015 | Fruhauf | A61N 1/36032 |
| 2005/0209657 A1 | 9/2005 | Chung et al. | 607/57 |
| 2009/0119096 A1* | 5/2009 | Gerl | G10L 21/0208 704/207 |
| 2010/0191309 A1 | 7/2010 | Schleich | 607/57 |
| 2011/0013791 A1* | 1/2011 | Griffin | H04R 25/356 381/317 |

OTHER PUBLICATIONS

Chen et al., *Effect of Individually Tailored Spectral Change Enhancement on Speech Intelligibility and Quality for Hearing-Impaired Listeners*, Proceedings of ICASSP 2013, Vancouver, Canada, 7 pages, May 26-31, 2013.

DiGiovanni et al., *Effects of Transient Noise Reduction Algorithms on Speech Intelligibility and Ratings of Hearing Aid Users*, American Journal of Audiology, vol. 20, pp. 140-150, Dec. 2011.

Ephraim et al., *Speech Enhancement Using a Minimum Mean-Square Error Short-Time Spectral Amplitude Estimator*, IEEE Transactions on Acoustics, Speech, and Signal Processing, vol. ASSP-32, No. 6, pp. 1109-1121, Dec. 1984.

Hernandez, *An Assessment of Everyday Noises and Their Annoyance*, Hearing Review, vol. 13, Issue 7, 10 pages, 2006.

Hochmair et al., *MED-EL Cochlear Implants: State of the Art and a Glimpse into the Future*, Trends in Amplification, vol. 10, No. 4, pp. 201-219. Dec. 2006.

Holden et al., *Speech Recognition With the Advanced Combination Encoder and Transient Emphasis Spectral Maxima Strategies in Nucleus 24 Recipients*, Journal of Speech, Language, and Hearing Research, vol. 48, No. 3, pp. 681-701, Jun. 2005.

Koning et al., *The Potential of Onset Enhancement for Increased Speech Intelligibility in Auditory Prostheses*, J Acoust. Soc. Am. vol. 132, Issue 4, pp. 2569-2581, Oct. 2012.

Stöbich, *Influence of Automatic Gain Control Parameter Settings on Speech Understanding of Cochlear Implant Users Employing the Continuous Interleaved Sampling Strategy*, Ear and Hearing, The Official Journal of the American Auditory Society, vol. 20, No. 20, pp. 104-116, Apr. 1999.

Vandali, *Emphasis of Short-Duration Acoustic Speech Cues for Cochlear Implant Users*, The Journal of the Acoustical Society of America, vol. 109, No. 5, pp. 2049-2061, May 2001.

International Searching Authority, International Search Report—International Application No. PCT/US2014/069323, dated Feb. 24, 2015, together with the Written Opinion of the International Searching Authority, 17 pages.

* cited by examiner

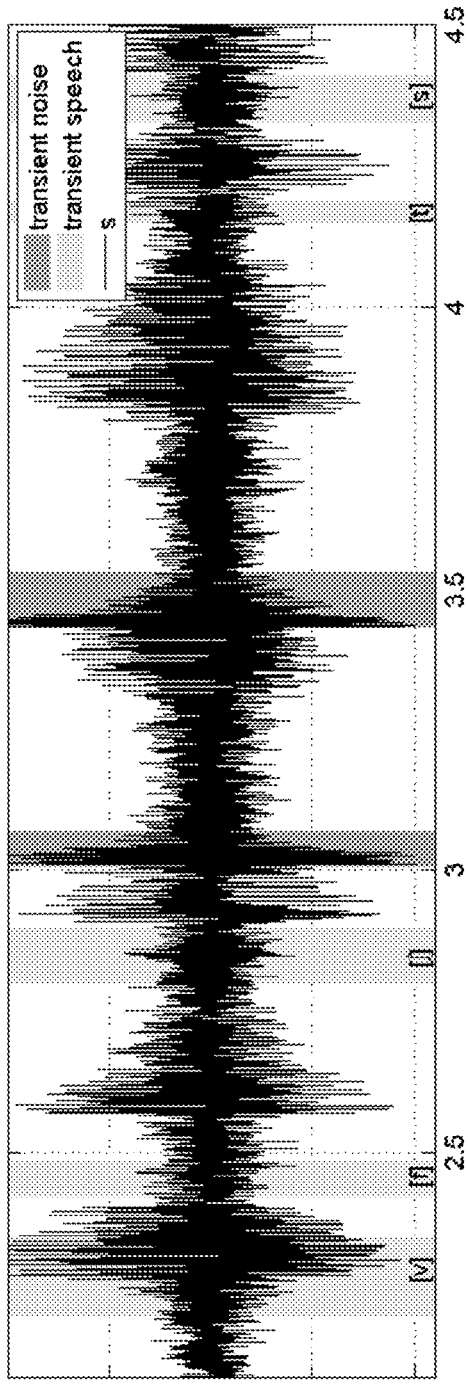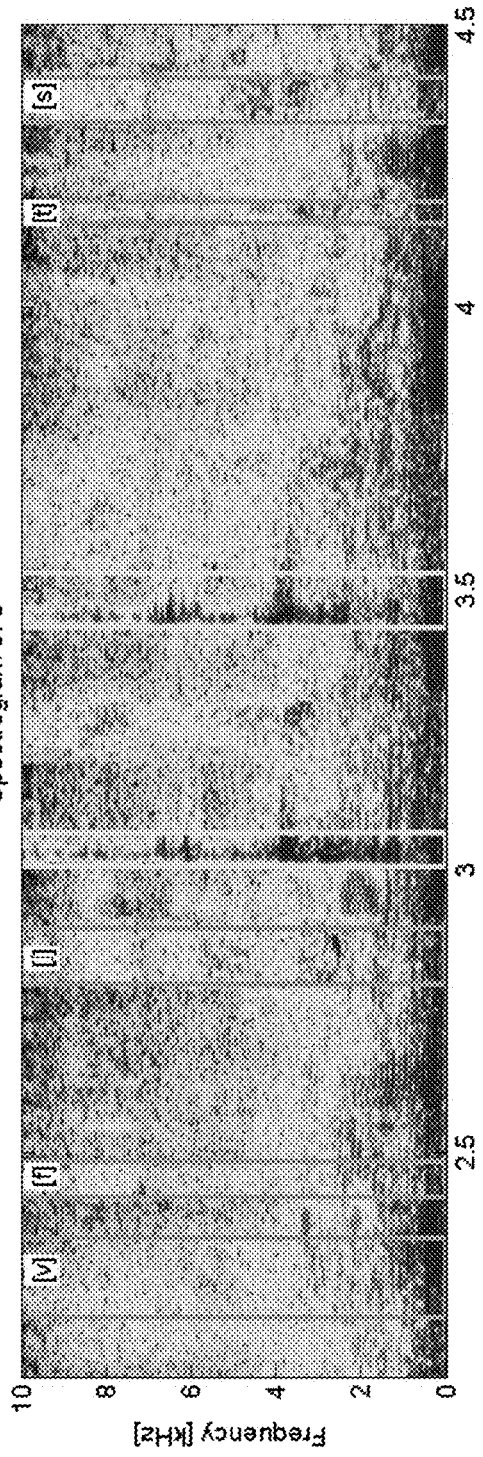

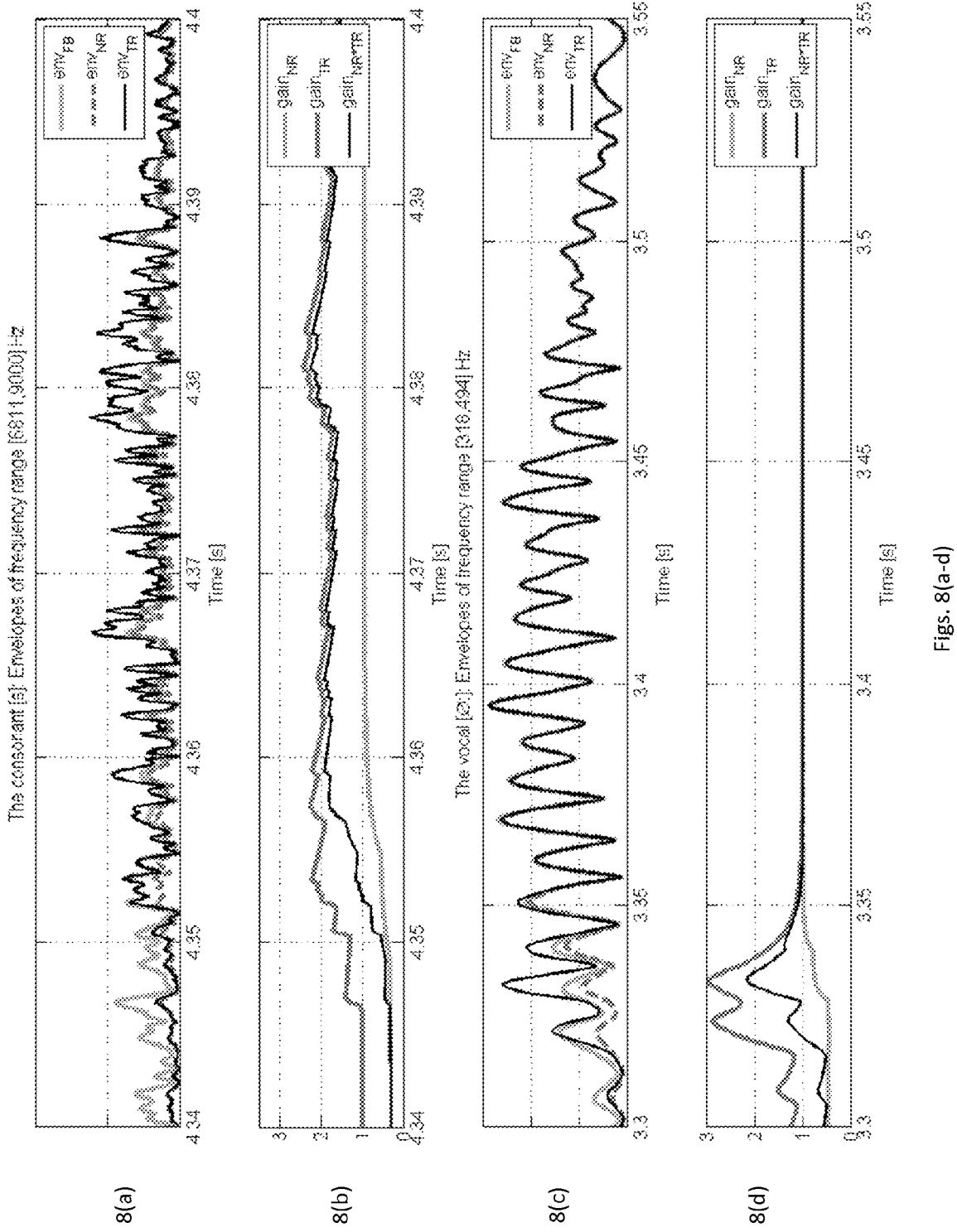
Figs. 8(a-d)

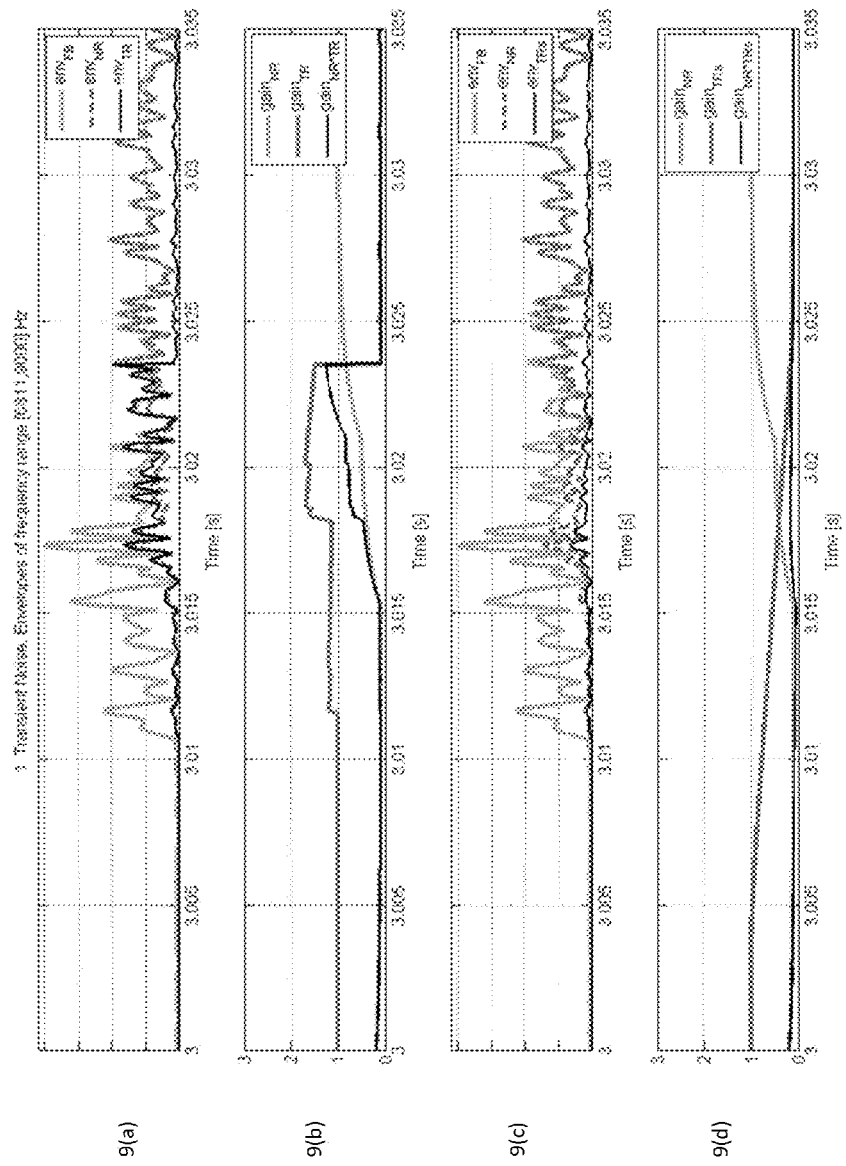
Figs. 9(a-d)

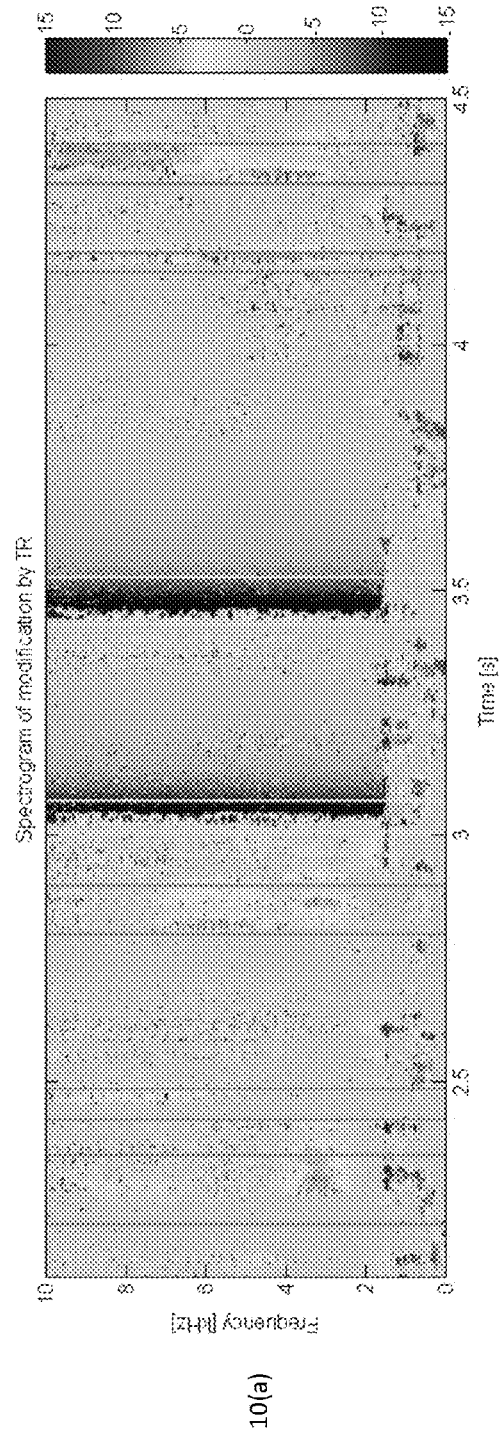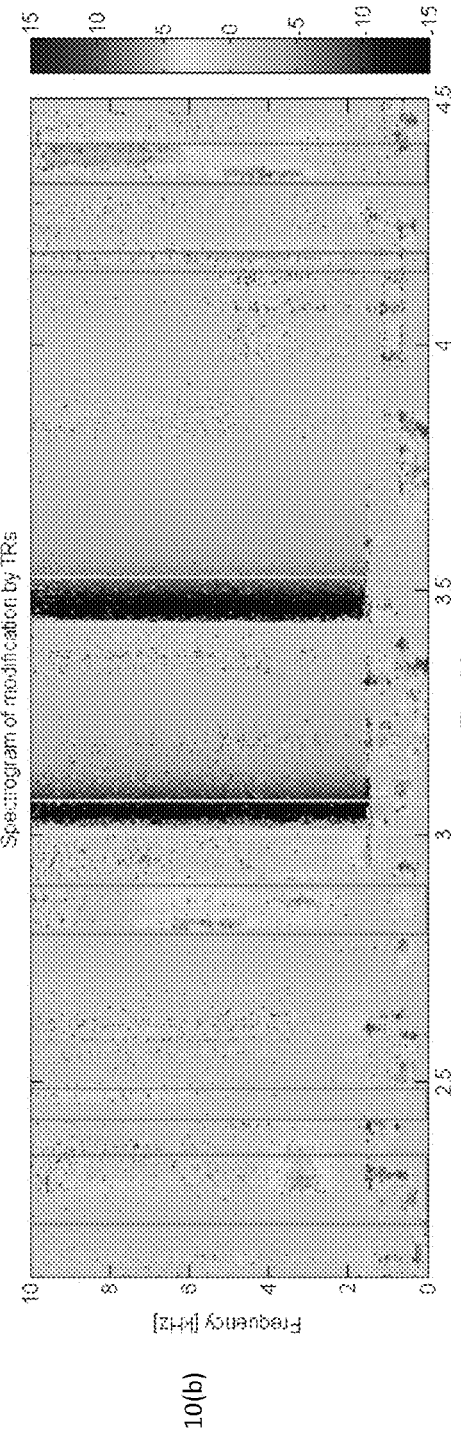
10(a)
10(b)
Figs. 10(a-b)

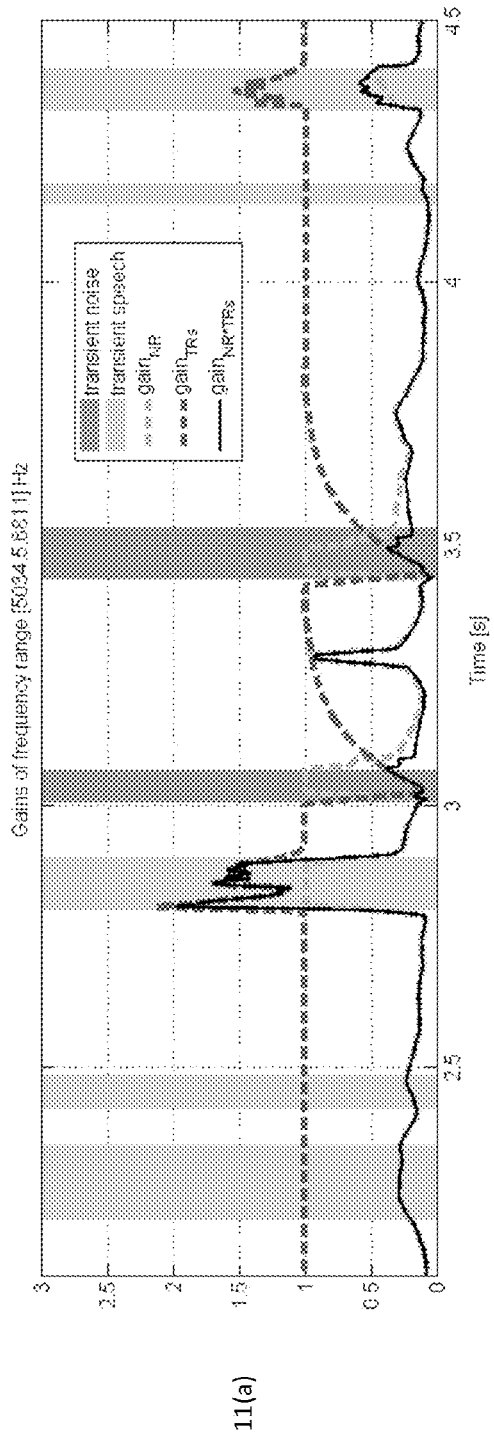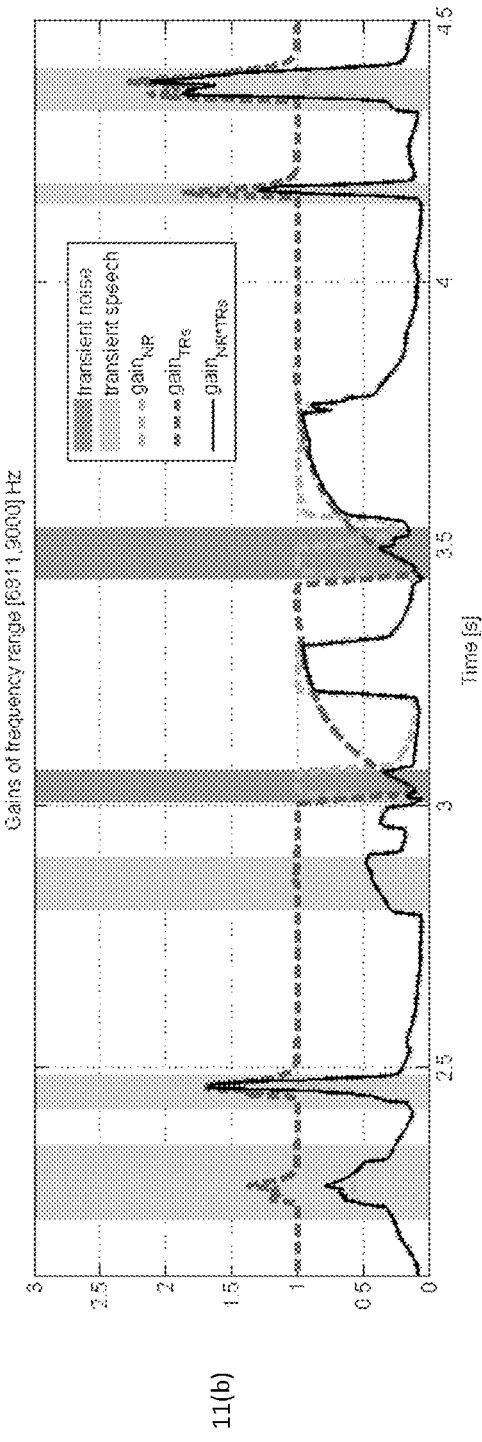
Figs. 11(a-b)

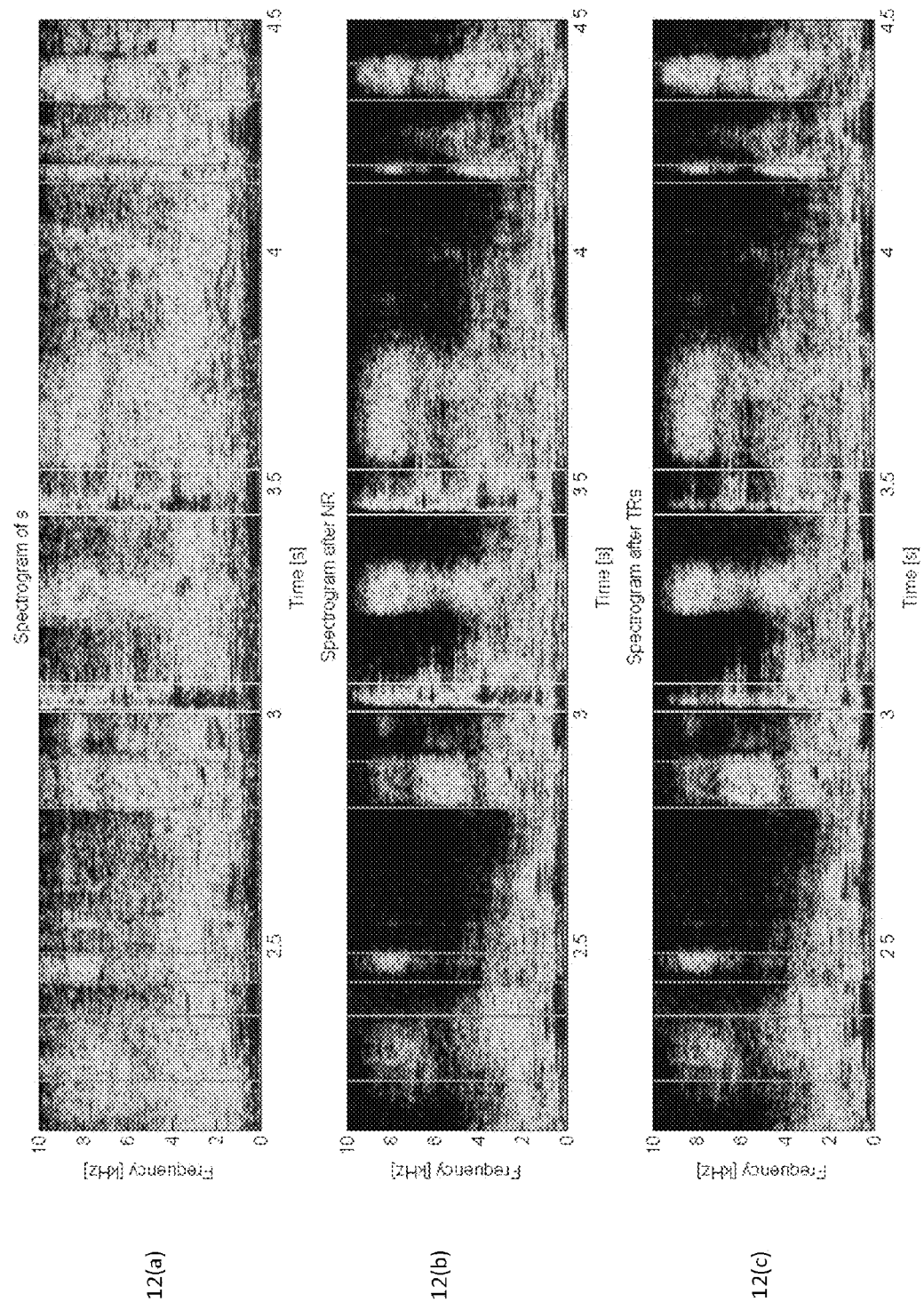
Figs. 12(a-c)

AUTOMATIC SELECTION OF REDUCTION OR ENHANCEMENT OF TRANSIENT SOUNDS

CROSS-REFERENCE TO RELATED APPLICATIONS

This application claims priority from U.S. Provisional Application No. 61/914,653 filed Dec. 11, 2013, entitled "Automatic Selection of Reduction or Enhancement of Transient Sounds," which is hereby incorporated herein by reference in its entirety.

TECHNICAL FIELD

The present invention relates to hearing implant systems such as cochlear implants, and specifically to the signal processing used therein associated with transient sounds.

BACKGROUND ART

A normal ear transmits sounds as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission via coil 107 into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple electrodes 112 on its surface that provide selective stimulation of the cochlea 104.

In cochlear implants today, a relatively small number of electrodes are each associated with relatively broad frequency bands, with each electrode addressing a group of neurons through a stimulation pulse the charge of which is derived from the instantaneous amplitude of the envelope within that frequency band. In some coding strategies, stimulation pulses are applied at constant rate across all electrodes, whereas in other coding strategies, stimulation pulses are applied at an electrode-specific rate.

Various signal processing schemes can be implemented to produce the electrical stimulation signals. Signal processing approaches that are well-known in the field of cochlear implants include continuous interleaved sampling (CIS) digital signal processing, channel specific sampling sequences (CSSS) digital signal processing (as described in U.S. Pat. No. 6,348,070, incorporated herein by reference), spectral peak (SPEAK) digital signal processing, and compressed analog (CA) signal processing. For example, in the CIS approach, signal processing for the speech processor involves the following steps:

(1) splitting up of the audio frequency range into spectral bands by means of a filter bank,
(2) envelope detection of each filter output signal,
(3) instantaneous nonlinear compression of the envelope signal (map law).

According to the tonotopic organization of the cochlea, each stimulation electrode in the scala tympani is associated with a band pass filter of the external filter bank. For stimulation, symmetrical biphasic current pulses are applied. The amplitudes of the stimulation pulses are directly obtained from the compressed envelope signals. These signals are sampled sequentially, and the stimulation pulses are applied in a strictly non-overlapping sequence. Thus, as a typical CIS-feature, only one stimulation channel is active at one time and the overall stimulation rate is comparatively high. For example, assuming an overall stimulation rate of 18 kpps and a 12 channel filter bank, the stimulation rate per channel is 1.5 kpps. Such a stimulation rate per channel usually is sufficient for adequate temporal representation of the envelope signal. The maximum overall stimulation rate is limited by the minimum phase duration per pulse. The phase duration cannot be chosen arbitrarily short, because the shorter the pulses, the higher the current amplitudes have to be to elicit action potentials in neurons, and current amplitudes are limited for various practical reasons. For an overall stimulation rate of 18 kpps, the phase duration is 27 µs, which is near the lower limit. Each output of the CIS band pass filters can roughly be regarded as a sinusoid at the center frequency of the band pass filter which is modulated by the envelope signal. This is due to the quality factor (Q≈3) of the filters. In case of a voiced speech segment, this envelope is approximately periodic, and the repetition rate is equal to the pitch frequency.

In the existing CIS-strategy, only the envelope signals are used for further processing, i.e., they contain the entire stimulation information. For each channel, the envelope is represented as a sequence of biphasic pulses at a constant repetition rate. A characteristic feature of CIS is that this repetition rate (typically 1.5 kpps) is equal for all channels and there is no relation to the center frequencies of the individual channels. It is intended that the repetition rate is not a temporal cue for the patient, i.e., it should be sufficiently high, so that the patient does not perceive tones with a frequency equal to the repetition rate. The repetition rate is usually chosen at greater than twice the bandwidth of the envelope signals (Nyquist theorem).

Another cochlear implant stimulation strategy that transmits fine time structure information is the Fine Structure Processing (FSP) strategy by Med-El. Zero crossings of the band pass filtered time signals are tracked, and at each negative to positive zero crossing a Channel Specific Sampling Sequence (CSSS) is started. Typically CSSS sequences are only applied on the first one or two most apical channels, covering the frequency range up to 200 or 330 Hz. The FSP arrangement is described further in Hochmair I, Nopp P, Jolly C, Schmidt M, Schößer H, Garnham C, Anderson I, *MED-EL Cochlear Implants: State of the Art and a Glimpse into the Future*, Trends in Amplification, vol. 10, 201-219, 2006, which is incorporated herein by reference.

FIG. 2 shows major functional blocks in the signal processing arrangement typical of existing cochlear implant (CI) systems wherein band pass signals containing stimulation timing and amplitude information are assigned to stimulation electrodes. Preprocessor Filter Bank 201 pre-processes an initial acoustic audio signal, e.g., automatic gain control, noise reduction, etc. Each band pass filter in the Preprocessor Filter Bank 201 is associated with a specific band of audio frequencies so that the acoustic audio signal is filtered into some N band pass signals, $B_1$ to $B_N$ where each signal corresponds to the band of frequencies for one of the band pass filters.

The band pass signals $B_1$ to $B_N$ are input to a Stimulation Pulse Generator 202 which extracts signal specific stimulation information—e.g., envelope information, phase information, timing of requested stimulation events, etc.—into a set of N stimulation event signals $S_1$ to $S_N$, which represent electrode specific requested stimulation events. For example, channel specific sampling sequences (CSSS) may be used as described in U.S. Pat. No. 6,594,525, which is incorporated herein by reference.

Pulse Mapping Module 203 applies a non-linear mapping function (typically logarithmic) to the amplitude of each band-pass envelope. This mapping function typically is adapted to the needs of the individual CI user during fitting of the implant in order to achieve natural loudness growth. This may be in the specific form of functions that are applied to each requested stimulation event signal $S_1$ to $S_N$ that reflect patient-specific perceptual characteristics to produce a set of electrode stimulation signals $A_1$ to $A_M$ that provide an optimal electric representation of the acoustic signal.

The Pulse Mapping Module 203 controls loudness mapping functions. The amplitudes of the electrical pulses are derived from the envelopes of the assigned band pass filter outputs. A logarithmic function with a form-factor C typically may be applied to stimulation event signals $S_1$ to $S_N$ as a loudness mapping function, which generally is identical across all the band pass analysis channels. In different systems, different specific loudness mapping functions other than a logarithmic function may be used, though still just one identical function is applied to all channels to produce the electrode stimulation signals $A_1$ to $A_M$ outputs from the Pulse Mapping Module 203.

Patient specific stimulation is achieved by individual amplitude mapping and pulse shape definition in Pulse Shaper 204 which develops the set of electrode stimulation signals $A_1$ to $A_M$ into a set of output electrode pulses $E_1$ to $E_M$ to the electrodes in the implanted electrode array which stimulate the adjacent nerve tissue.

Background noise reduces speech intelligibility of hearing aid and cochlear implant users. According to Hernandez et al., *An Assessment Of Everyday Noises And Their Annoyance*, Hearing Review, 2006, 13(7), 16-20 (incorporated herein by reference), 33% of sensate background noise is formed by transient sounds such as computer key strokes, slamming doors, dish clattering, etc., all of which are unpleasant and reduce listening comfort (See also, German Patent DE 102005043314, incorporated herein by reference). The transient noise reduction algorithms in existing hearing aids such as the AntiShock from Unitron Connect and the SoundSmoothing from Siemens have been found to yield an improvement in the listening experience. See DiGiovanni et al., *Effects of Transient-Noise Reduction Algorithms on Speech Intelligibility and Ratings of Hearing Aid Users*, American Journal of Audiology, first published on Sep. 22, 2011 as doi:10.1044/1059-0889(2011/10-0007), incorporated herein by reference. Transient noise reduction is also sought in other applications. For example, sound quality for car passengers may be improved by reducing the transient road noise created when tires strike an obstruction. See U.S. Pat. No. 7,725,315, incorporated herein by reference.

On the other hand, enhancement of short-duration transient speech features, like consonants or on/offsets of speech, may improve speech perception in certain listening conditions, particularly with regard to low intensities. See: Vandali A. E., *Emphasis of Short-duration Acoustic Speech Cues for Cochlear Implant Users*, The Journal of the Acoustical Society of America, 2001, 109(5), 2049-2061, doi: 10.1121/1.1358300; and Holden L. K., Vandali A. E., Skinner M. W., Fourakis M. S., Holden T. A., *Speech Recognition With the Advanced Combination Encoder and Transient Emphasis Spectral Maxima Strategies in Nucleus 24 Recipients*, Journal of Speech, Language, and Hearing Research, 2005, 48, 681-701, each of which is incorporated by reference in its entirety. This may also enhance the onset of certain speech features, ultimately yielding increased intelligibility. See Koning R., Wouters J., *The Potential of Onset Enhancement for Increased Speech Intelligibility in Auditory Prostheses*, J. Acoust. Soc. Am. 132(4), October 2012, 2569-2581; and Jing Chen and Brian C. J. Moore, *Effect of Individually Tailored Spectral Change Enhancement on Speech Intelligibility and Quality for Hearing-Impaired Listeners*, Proceedings of ICASSP 2013, Vancouver, Canada, May 2013, each of which incorporated herein by reference).

Likewise, in high-end audio equipment that renders audio data, the potential to modify transient features like drumsticks hitting a drum is desired to meet different individual preferences in music listening. See U.S. Pat. No. 7,353,169, incorporated herein by reference. In U.S. Pat. No. 7,353,169, the spectral flux is used to determine frequency-specific indicators of transient features in high end audio equipment. According to these indicators, a modification of the corresponding transient features is applied to improve the impression of music. It is up to the user to decide on the amount, the frequency ranges, and the kind of modification (suppression or enhancement) he prefers.

Some methods aiming for separate reduction and enhancement of transients are provided below.

Transient Noise Reduction

In U.S. patent application Ser. No. 13/975,487, entitled "Reduction of Transient Sounds in Hearing Implants", from Frühauf, filed Aug. 26, 2013 (incorporated herein by reference), the sound signal is transformed into K sub-signals and each of these signals corresponds to a certain frequency range. The envelopes of these sub-signals are considered and referred to as subband envelopes. One characteristic of a transient noise signal are envelopes having high values in each channel over a wide frequency range, where the lower frequency bound is above approx. 1 kHz. Channel specific indicators of a transient noise feature are calculated using the power of the input signal and the envelopes in the subbands. These indicators have high values if all the corresponding subband envelopes have high values relative to the power of the whole signal. High values of all indicators in the frequency range above approx. 1 kHz characterize a transient noise feature, while consonants or fricatives only have some indicators with high values. Thus the indicators of the frequency ranges above approx. 1 kHz are multiplied to get an indicator that has a large value for a transient noise feature.

Another characteristic of transient signals are a fast and steep rising envelope of the sound signal. Thus during the occurrence of a transient, the envelope has much larger values for a short time interval. In German Patent DE 102005043314, the steepness and/or the amplitude of the envelope of the sound signal are considered. If one or both of these values exceed certain thresholds, the sound signal is attenuated.

In European Patent EP 1371263 (incorporated herein by reference), the sound signal is transformed into K sub-signals in the frequency domain. Then, for each sub-signal, two or three sub-indices are calculated which are used to classify the present sound signal into the categories "stationary noise", "quasi stationary noise", "desired speech and music" and "transient noise". These sub-indices refer to intensity changes during a given time interval, the modulation frequency, and the duration of very similar intensities of the signal, respectively. According to the classified category, a gain function is calculated, that is used to suppress transient sounds or to enhance the SNR in case of the classified categories "stationary noise" or "quasi stationary noise".

In WO 99/53615 (incorporated herein by reference), a transient detector divides the input signal into at least two frequency bands. In each of these bands, the derivative and/or the amplitude of the envelope are compared to at least one threshold function to indicate a transient in the respective band. If a transient is detected in at least one band, the coefficients of an adaptive filter are changed in such a way that the transients in the input signal are reduced by filtering the delayed input signal with this determined adaptive filter. After the detector no longer detects a transient, the filter coefficients return to the values before the transient has appeared.

In U.S. Pat. No. 7,353,169, the spectral flux is used to determine frequency-specific indicators of transient features in high end audio equipment. According to these indicators, a modification of the corresponding transient features is applied to improve the impression of music. It is up to the user to decide on the amount, the frequency ranges, and the kind of modification (suppression or enhancement) he prefers.

U.S. Pat. No. 7,725,315 (incorporated herein by reference), describes using models of transient road noise based on a code book or a neural network to attenuate transient sounds.

U.S. Pat. No. 7,869,994 (incorporated herein by reference) describes an attenuation of certain wavelet coefficients based on a threshold to suppress transient sounds.

A possibility to reduce transient features in a cochlear implant system is to use hearing aid algorithms as proposed in U.S. 2005/0209657 (incorporated herein by reference).

In Stöbich B., Zierhofer C. M., Hochmair E. S., *Influence of Automatic Gain Control Parameter Settings on Speech Understanding of Cochlear Implant Users Employing the Continuous Interleaved Sampling Strategy*" Ear & Hearing, 1999, 20, 104-116 Stöbich 1999 (incorporated herein by reference), a dual front-end AGC is proposed to reduce transient features.

Transient Speech Enhancement

U.S. Pat. No. 7,219,065 (incorporated herein by reference) describes that a plurality of envelopes in the frequency channels of the sound signal are generated. Then, in each channel, changes of the envelope-intensities within a short time window (60 ms) are investigated to calculate a gain, which is used to enhance the envelope intensity in case a transient speech feature gets detected. For small variations or decreasing values of the intensities, the gain is set to one. The highest gain values (up to 14 dB) are achieved if the intensities have low, high and low values in the beginning (0-20 ms), in the middle (20-40 ms), and at the end (40-60 ms) of the time window, respectively. Furthermore, a small enhancement is used if there is an onset, i.e., small values of the envelopes in the beginning, followed by a high value in the middle and at the end of the time window.

Koning R., Wouters J., *The Potential of Onset Enhancement for Increased Speech Intelligibility in Auditory Prostheses*, J. Acoust. Soc. Am. Volume 132, Issue 4, pp. 2569-2581 (2012); (incorporated herein by reference) describes a sound signal separated into frequency bands, and the onsets of the corresponding envelopes are enhanced by adding peak envelope signals. Band-specific peak envelopes are the weighted rectified differences of the corresponding envelope and the weighted low-passed filtered envelope. Studies have shown that this enhancement of the onsets increases speech intelligibility.

Chen, J., Moore, B. C. J., *Effect of Individually Tailored Spectral Change Enhancement on Speech Intelligibility and Quality for Hearing-impaired Listeners*, Proceedings of ICASSP 2013, Vancouver, Canada, May 2013 (incorporated herein by reference) investigates the influence of enhancement of spectral changes for hearing impaired listeners. The input sound signal is transformed into spectral components by a short time Fourier transformation. Changes of these amplitudes are then enhanced and back-transformed to the time domain. These enhanced signals are evaluated by subjects with mild to moderate hearing loss. The study shows that the speech intelligibility increases while the sound quality remains nearly the same.

SUMMARY OF THE EMBODIMENTS

In accordance with an embodiment of the invention, a method of generating electrode stimulation signals for electrode contacts in an electrode array associated with a hearing implant is presented. An input audio signal is processed to generate a plurality of band pass channel signals each representing an associated band of audio frequencies. A stationary noise reduction is applied so as to provide a stationary noise reduced channel envelope from each channel signal. A transient in one or more of the channel envelopes is detected. The channel envelopes are modified as a function of whether the transient is transient noise or transient speech, so as to form transient modified envelopes. The transient modified envelopes are used to generate electrode stimulation signals to the electrode contacts.

In accordance with related embodiments of the invention, the method may include reducing the transient noise in one or more of the channel envelopes, if the transient is transient noise, so as to form the transient modified envelopes. Alternatively, if the transient is transient speech, the transient speech in one or more of the channel envelopes is enhanced to form the transient modified envelopes. The hearing implant may be a totally implantable cochlear implant, a cochlear implant having both an external speech processor and an implanted stimulator that includes the electrode array, or an auditory brainstem implant.

In accordance with further related embodiments of the invention, detecting the transient may include determining for each channel envelope a channel-specific transient noise indicator characterizing transient noise present in the channel signal, and determining for each channel envelope a channel-specific transient speech indicator characterizing transient speech present in the channel signal. The channel-specific transient noise indicator may be based on a proportion of power of the channel envelope to power of the input audio signal. Determining the channel-specific transient noise indicator may include high-pass filtering the channel envelope. Determining for each channel envelope a channel-specific transient speech indicator may include: high-pass filtering the channel envelope; low-pass filtering the channel envelope; determining ranges of the high-pass filtered channel envelope, the low-pass filtered channel envelope, and the channel envelope; and determining for each channel envelope a channel-specific transient speech indicator as a function of the determined ranges. Modifying the channel envelopes may include applying a channel-specific gain to each channel envelope as a function of their associated transient noise indicator and transient speech indicator to produce the transient modified envelopes. A time delay may be introduced, that upon detection of transient noise, allows modification of the applied channel-specific gain up to a predetermined time prior to the detected transient noise. Modifying the channel envelopes may include limiting amplitude of the channel envelopes to reduce distortion resulting from a large enhancement.

In accordance with another embodiment of the invention, a signal processing arrangement is provided for generating electrode stimulation signals for electrode contacts of an electrode array associated with a hearing implant. The arrangement includes a filter bank pre-processor configured to process an input audio signal to generate a plurality of band pass channel signals each representing an associated band of audio frequencies. A stationary noise reduction (NR) module is configured to reduce stationary noise in each channel and provide a stationary noise reduced channel envelope from each channel signal. A transient modification stage (TMS) is configured to detect a transient in one or more of the channel envelopes, and modify the channel envelopes as a function of whether the transient is transient noise or transient speech, so as to form transient modified envelopes. A stimulation signal generator is configured to use the transient modified envelopes to generate electrode stimulation signals to the electrode contacts.

In accordance with related embodiments of the invention, the transient modification stage may be configured such that if the transient is transient noise, reduce the transient noise in one or more of the channel envelopes to form the transient modified envelopes. If the transient is transient speech, the transient speech in one or more of the channel envelopes is enhanced to form the transient modified envelopes. The hearing implant may be a totally implantable cochlear implant, a cochlear implant having both an external speech processor and an implanted stimulator that includes the electrode array, or an auditory brainstem implant.

The transient modification stage may determine for each channel envelope a channel-specific transient noise indicator characterizing transient noise present in the channel signal, and a channel-specific transient speech indicator characterizing transient speech present in the channel signal. The transient modification stage may determine the channel-specific transient noise indicator based on a proportion of power of the channel envelope to power of the input audio signal. The transient modification stage may determine the channel-specific transient noise indicator based on high-pass filtering the channel envelope. The transient modification stage may include a high-pass filter for filtering the channel envelope, and a low-pass filter for filtering the channel envelope, wherein the transient modification stage is further configured to determine ranges of the high-pass filtered channel envelope, the low-pass filtered channel envelope, and the channel envelope, and determine for each channel envelope a channel-specific transient speech indicator as a function of the determined ranges. The transient modification stage may be further configured to apply a channel-specific gain to each channel envelope as a function of their associated transient noise indicator and transient speech indicator to produce the transient modified envelopes. The transient modification stage may be configured to provide a time delay that, upon detection of transient noise, allows modification of the applied channel-specific gain up to a predetermined time prior to the detected transient noise. The transient modification stage may be configured, when modifying the channel envelopes, to limit amplitude of the channel envelopes to reduce distortion resulting from a large enhancement.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing features of embodiments will be more readily understood by reference to the following detailed description, taken with reference to the accompanying drawings, in which:

FIG. 3(a) shows an exemplary input sound signal that includes both noise and speech transients; while FIG. 3(b) shows its associated spectrogram;

FIG. 8(a-d) show envelopes and corresponding gains for various speech transients, in accordance with an embodiment of the invention. FIG. 8(a) shows the envelopes for a speech transient that includes the consonant [s], while in FIG. 8(b), the corresponding gains are shown. FIG. 8(c) shows the envelopes for a speech transient that includes the vocal [ø:], while in FIG. 8(b), the corresponding gains are shown;

FIG. 9(a) shows transient noise envelopes, while 9(b) shows the corresponding gains, in accordance with an embodiment of the invention. FIGS. 9(c) and 9(d) show the corresponding envelopes and gains, respectively, in which a linear interpolation of the gain is applied between the gain value 20 ms before and at location of the detection of the transient noise, in accordance with an embodiment of the invention;

FIG. 10(a) shows a spectrogram of the signal-changes of the TMS, in accordance with an embodiment of the invention. FIG. 10(b) shows a spectrogram of the signal-changes of the TMSs, in accordance with various embodiments of the invention; and FIG. 11(a) shows the resulting gain within the frequency range of 5034.5-6811 Hz corresponding to the input sound signal s, in accordance with an embodiment of the invention. FIG. 11(b) shows the resulting gain within the frequency range of 6811-9000 Hz corresponding to the input sound signal s, in accordance with an embodiment of the invention.

FIG. 12(a) shows a spectrogram associated with input signal s after the filter bank, in accordance with an embodiment of the invention. FIG. 12(b) shows a spectrogram associated with the input signal s after the stationary noise reduction, in accordance with an embodiment of the invention. FIG. 12(c) shows a spectrogram associated with the input signal s after transient modification, in accordance with an embodiment of the invention.

DETAILED DESCRIPTION OF SPECIFIC EMBODIMENTS

In illustrative embodiments, a system and methodology is provided that is directed to improving hearing comfort and speech intelligibility in users of hearing aids or hearing implants, such as cochlear implants. More particularly, in various embodiments a detector of transient sounds may automatically characterize transients as noise or as a speech feature. The automatic assignment of transient features advantageously allows for a reduction of unpleasant transient noise such as dish clattering, paper rustling, or door slamming, and the enhancement of desirable sound features such as speech or music onsets. This may lead to an increase of the speech intelligibility and the hearing comfort of hearing implant users. Details are discussed below.

FIG. 3(a) shows an exemplary input sound signal that includes both noise and speech; while FIG. 3(b) shows its associated spectrogram. The input sound signal includes speech, babble noise, and two transient noise sounds due to dish clatter. These transient noise sounds are marked by the dark grey areas, and are unpleasant for hearing aid/implant users and should be reduced. On the other hand, there are transient speech features with low intensities which are marked by the light grey areas. In FIG. 3(b) the phonetic transcriptions are labeled in brackets. Here, the transient speech features are the consonants [v] and [f] of the name "Wolfgang" ([volfgang]), [ʃ] of the word "schenkt" ([ʃenkt]) and [t] and [s] of the word "Tasse" ([tase]), respectively. In FIG. 3(b), the transient features are marked by the dark (speech transient) and light grey lines (transient noise).

Figure 1:
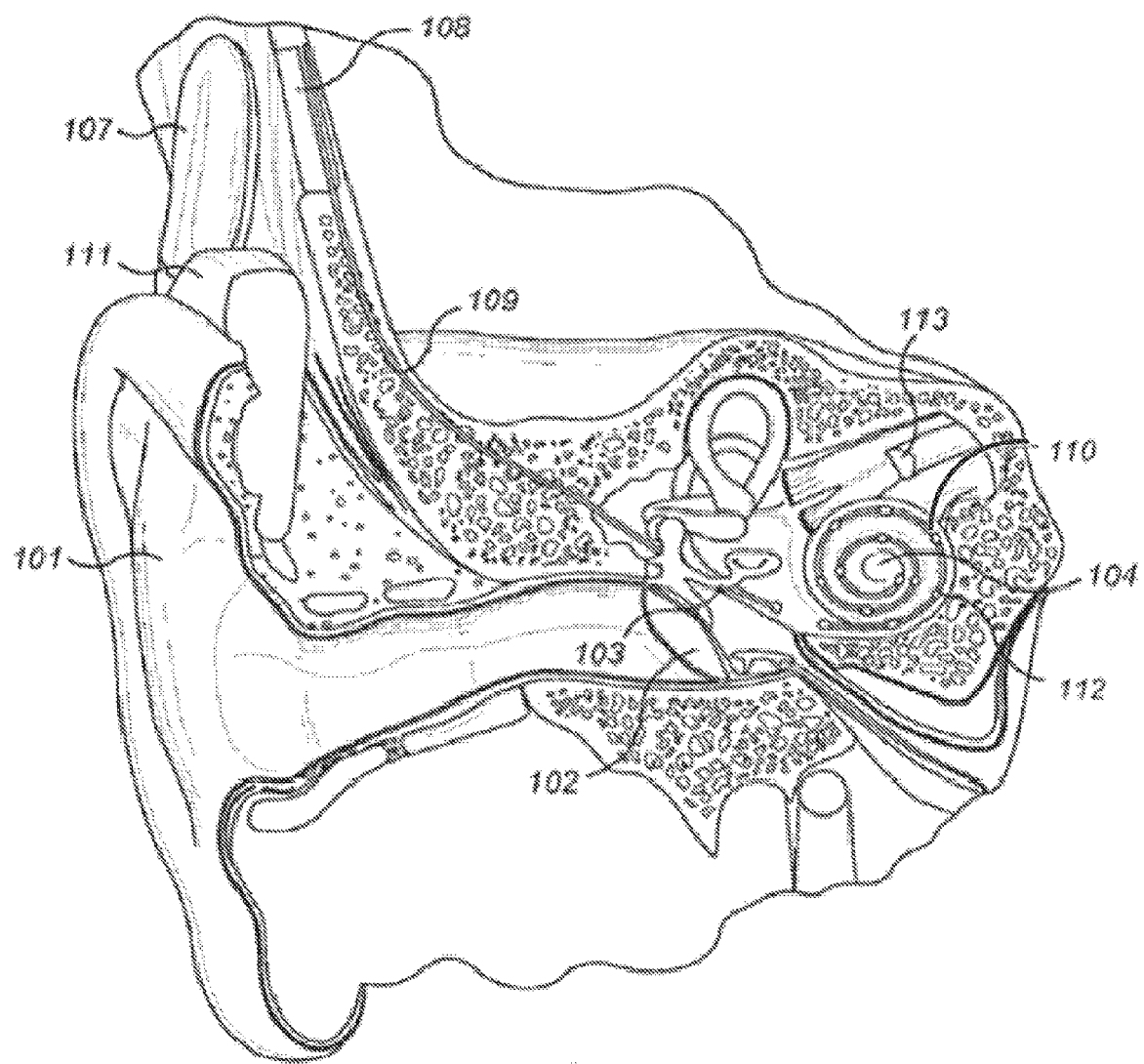
FIG. 1 shows the anatomy of a typical human ear and components in a cochlear implant system.
Figure 2:
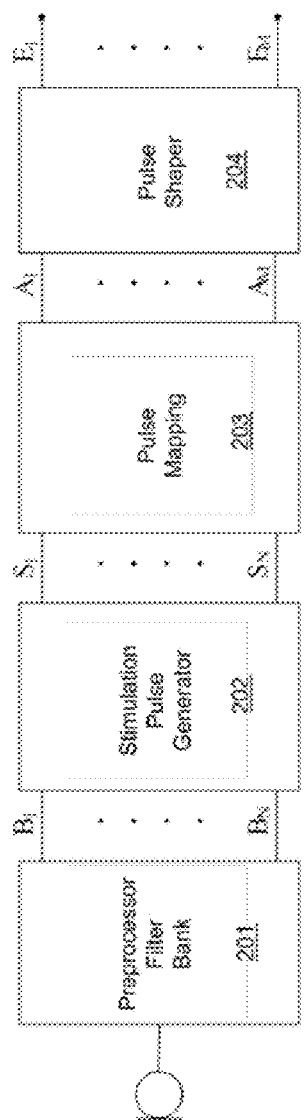
FIG. 2 shows major signal processing blocks of a typical cochlear implant system.
Figure 4:
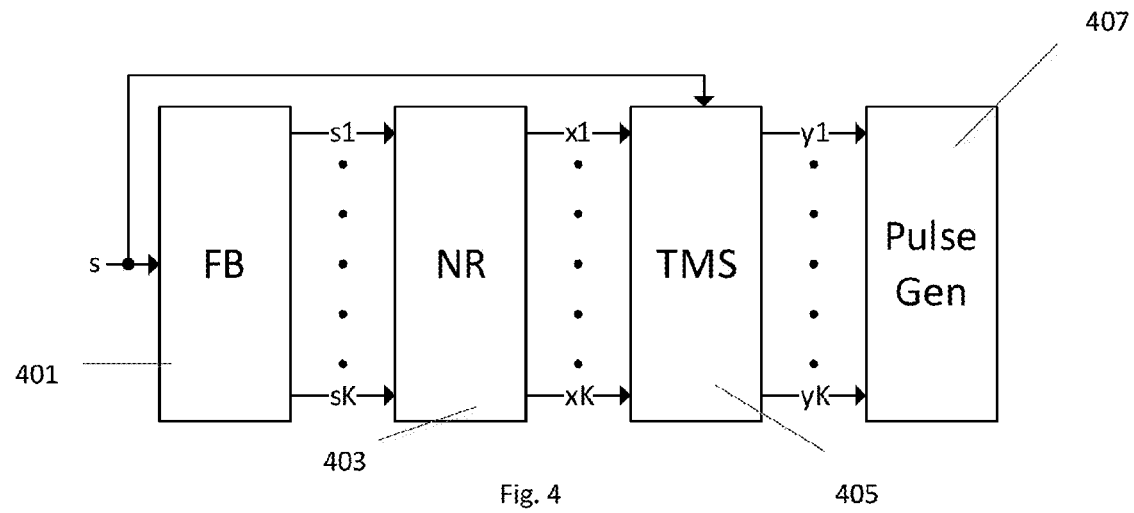
FIG. 4 shows a general schematic of a signal processing system for a hearing aid or an implant, in accordance with an embodiment of the invention.

FIG. 4 shows a general schematic of a signal processing system for a hearing aid or an implant, in accordance with an embodiment of the invention. The hearing implant may be, without limitation, a cochlear implant, in which the electrodes of a multichannel electrode array are positioned such that they are, for example, spatially divided within the cochlea. The cochlear implant may be partially implanted, and include, without limitation, an external speech/signal processor, microphone and/or coil, with an implanted stimulator and/or electrode array. In other embodiments, the cochlear implant may be a totally implanted cochlear implant. In further embodiments, the multi-channel electrode may be associated with a brainstem implant, such as an auditory brainstem implant (ABI).

The signal processing system shown in FIG. 4 includes a single channel stationary noise reduction (NR) module 403 and a subsequent transient modification stage (TMS) 405. Here, we start with a digitized sound signal s. Then, s is divided into K analytic signals $s_1, \ldots, s_K$ by a filter bank (FB) 401, which assigns a corresponding frequency range to each of them. The filter bank (FB) 401 may be implemented as multiple bandpass filters with specific cut-off frequencies, or alternatively and without limitation, a fast Fourier transform (FFT) or a short-time Fourier transform (STFT). Next, the noise reduction (NR) module 403 reduces the stationary noise in each channel. The output of the noise reduction (NR) module 403 are K envelopes $x_1, \ldots, x_K$ with reduced stationary noise. A possible implementation of this module can be found in: Y. Ephraim, D. Malah, *Speech Enhancement Using a Minimum Mean-Square Error Short-Time Spectral Amplitude Estimator*, IEEE Transactions on Acoustic, Speech, and Signal Processing, Vol. ASSP-32, No. 6, December 1984; and, S. F. Boll, *Suppression of Acoustic Noise in Speech using Spectral Subtraction*, IEEE Trans. Acoustics, Speech, and Sig. Proc., Vol. ASSP 27, No. 2, April 1979, each of which is incorporated herein by reference. These K envelopes are the input signals to the transient modification stage (TMS) 405. In TMS 405, the transient features in each envelope are modified according to the kind of detected transient. For example, a detected transient noise may be reduced, while a detected transient speech feature or other desirable sound feature, such as, without limitation, a musical onset, may be enhanced. This results in an additional modification of the envelopes, which are the input signals $y_1, \ldots, y_K$ to the pulse generator module 407. The generated pulses are then transmitted to the hearing aid or implant.

Figure 5:
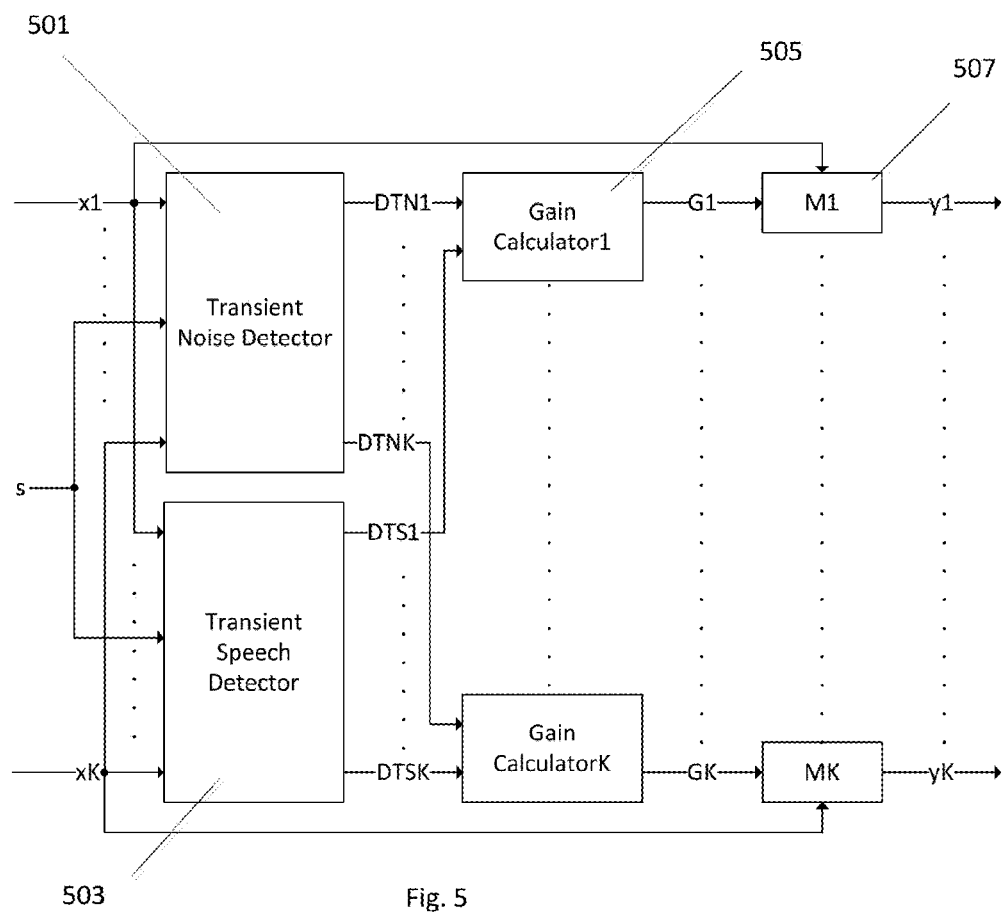
FIG. 5 shows an exemplary TMS in more detail, in accordance with an embodiment of the invention.

FIG. 5 shows an exemplary transient modification stage TMS 405 in more detail, in accordance with an embodiment of the invention. The TMS may include, for example, a transient noise detector module 501, a transient speech detector module 503, gain calculator modules 505, and gain application modules M1, ..., MK 507 in which the calculated gains are applied to the envelopes $x_1, \ldots, x_K$. Each of these is addressed below.

Transient Noise Detector Module

The input signals of the transient noise detector module 501 may include the K envelopes $x_1, \ldots, x_K$ and the sound signal s. The output of this module may include, for example, the indicator signals $DTN_1, \ldots, DTN_K$ of transient noise for each channel. If a transient noise feature exists at time t, the indicators may have, without limitation, high values, whereas if transient noise is absent, the indicators may have low values. Exemplary methods to calculate transient noise indicators that may be used are described above in the background section. Illustratively, the methods may include the following.

A. Let the normalized envelopes be the value of each envelope compared with all envelopes or the energy of the input signal s, i.e., $$\hat{x}_k = \frac{x_k}{LP(s)},$$

where LP(s) is a power estimation of the whole audio signal. Then, a combination of some of the normalized envelopes may be used as indicator of transient noise; since the envelopes have high values in most frequencies at the locations of a transient noise in contrast to transient speech features (see FIG. 3(b)). A possible calculation is given by $$DTN_k = \prod_{m \in S} \hat{x}_m$$

where S is the set of channels with lower frequency boundary above approx. 1 kHz. For a more detailed description of an illustrative algorithm see Frühauf.

B. A combination of the envelopes may be used as indicator instead of normalized envelopes.

C. Combinations of high-pass filtered envelopes or normalized envelopes may be used to determine the indicators.

Transient Speech Detector Module

Figure 6:
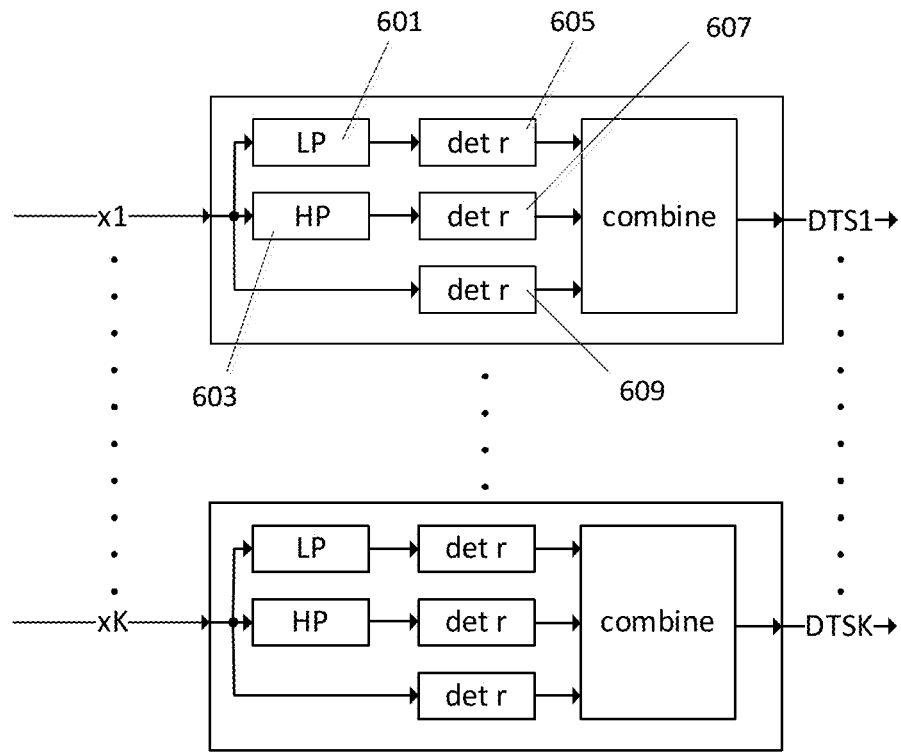
FIG. 6 shows an exemplary implementation of the transient speech detector module, in accordance with an embodiment of the invention.

The transient speech detector module 503 may include the same input signals $x_1, \ldots, x_K$ as the transient noise detector module 501 and may further include signal s. Output signals of the transient speech detector module 503 may include indicator signals $DTS_1, \ldots, DTS_K$ of transient speech. An exemplary implementation of the transient speech detector module 503 is shown in FIG. 6, in accordance with an embodiment of the invention. The calculation of the indicators may be done in each channel separately. For the sake of simplicity, the subindex $_k$ will be neglected in the discussion below.

In a first step, the input signal x may be low-pass filtered in the module LP 601 and high-pass filtered in the module HP 603. In a second step a distinct range is determined for the signals LP(x), HP(x) and x with any suitable bounded discrete or continuous function separately in range determination modules 605, 607 and 609, respectively, by for example r(v)=max(0, a−|m−v|), where v can be LP(x), HP(x) or x. The parameters a and m may be chosen for each channel and the low- ($a_{LP}$, $m_{LP}$) and high-pass ($a_{HP}$, $m_{HP}$) filtered signals and the signal x($a_x$, $m_x$) differently. In a third step, the three signals r(LP(x)), r(HP(x)) and r(x) are combined to achieve the output signal DTS. The combination may be done, without limitation, by multiplication or a look-up table or where the distinct range output is binary—any logic-combination comprising logic AND or logic OR gates. A transient speech feature may be a transient onset or transient offset speech feature and may be detected if $m_{LP}-a_{LP}$<LP(x)<$m_{LP}+a_{LP}$ and $m_{HP}-a_{HP}$<HP(x)<$m_{HP}+a_{HP}$ and $m_x-a_x$<x<$m_x+a_x$. This yields an indicator having large values if a transient speech feature (for example an onset of speech) occurs in the corresponding channel, with an indicator having low values if there is no transient speech feature. This is the case since, for example:

The high-pass filtered signals have small absolute values for stationary signals.

During a vowel, a transient noise feature, or a consonant the mean value of x is large, i.e., LP(x)>$m_{LP}+a_{LP}$.

In general, speech is in the dynamic range from 50 to 70 dB sound pressure level (spl). Thus the transient speech features are in a certain interval of x.

The onset of a transient noise is very steep and thus the absolute value of the high-pass filtered signal is large, i.e., HP(x)>$m_{HP}+a_{HP}$ or HP(x)<$m_{HP}-a_{HP}$.

In another embodiment the signal LP(x) in step 2 may be further high-pass filtered to form signal HP(LP(x)) before feed to range determination module 605. A transient onset feature is detected if HP(LP(x)) is within an interval {v:r(v)>0, v=HP(LP(x))}=]$m_{on}-a_{on}$, $m_{on}+a_{on}$[ ⊂ ]0, +∞[ and a transient offset speech feature is detected if HP(LP(x)) is within an interval {v:r(v)>0, v=HP(LP(x))}=]$m_{off}-a_{off}$, $m_{off}+a_{off}$[ ⊂ ]−∞, 0[ and further $m_{LP}-a_{LP}$<LP(x)<$m_{LP}+a_{LP}$ and $m_{HP}-a_{HP}$<HP(x)<$m_{HP}+a_{HP}$ and $m_x-a_x$<x<$m_x+a_x$ is fulfilled. The parameters $a_{on}$, $m_{on}$ and $a_{off}$, $m_{off}$ define the interval boundaries for the onset and offset transient speech feature in the same way as for the parameters $a_{LP}$, $m_{LP}$ and $a_{HP}$, $m_{HP}$ and $a_x$, $m_x$, respectively. The parameters a and m may be chosen for each channel and the onset ($a_{on}$, $m_{on}$) and offset ($a_{off}$, $m_{off}$) signals differently. $r_{on}$=r(HP(LP(x))) and $r_{off}$=r(HP(LP(x))) denote the signal output by the range determination module 605 for onset and offset speech feature, respectively. In the third step, the four signals max($r_{on}$, $r_{off}$), r(LP(x)), r(HP(x)) and r(x) are combined to achieve the output signal DTS. The combination may be done, without limitation, by multiplication.

Thus, generally during onsets and offset of speech features does DTS have values not equal to zero. The parameters $a_x$, $m_x$ and $a_{LP}$, $m_{LP}$ and $a_{HP}$, $m_{HP}$ and $a_{on}$, $m_{on}$ and $a_{off}$, $m_{off}$ are chosen according the empirically found thresholds of the speech in the way that the transient noise feature can be reliably distinguished from the speech signal. These thresholds may depend on the language. The parameters may also depend on the frequency, i.e., vary over the channel, preferably having higher values at low frequency channels than at high frequency channels. The parameters may depend further on the input signals, for example may depend on whether or not the input signal comprises a normalized envelope. The parameters may depend on any combination of the language, the frequency channel and/or the input signal. The parameters may be programmed into the external signal processor 111 and/or implant 108 of the cochlear implant system during the fitting session. Exemplary methods to calculate the speech transient indicators that may be used are described above in the background section.

Gain Calculator Module

Figure 7:
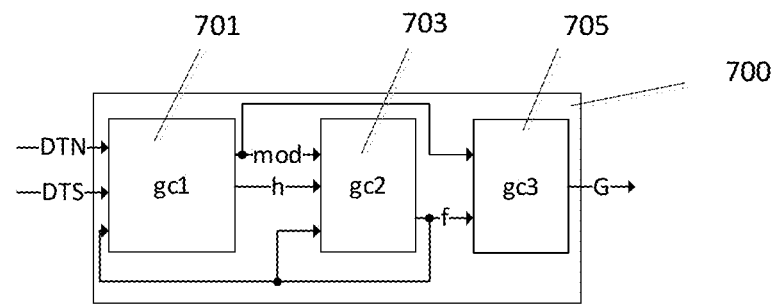
FIG. 7 shows an exemplary implementation of a gain calculator module, in accordance with an embodiment of the invention.

The gain calculator module 505 may include the indicators of transient noise $DTN_k$ and speech $DTS_k$ as input signals. The output may be a channel-specific gain $G_k$. FIG. 7 shows an implementation of a gain calculator module 700 that may be separated into three parts, in accordance with an embodiment of the invention. A first module "gc1" 701 generates an actual gain function h and the actual active mode (mod ∈ {enh,sup}) for enhancement or suppression of the signal. The second module "gc2" 703 calculates a signal f ∈ [0,1], which defines the amount of suppression or enhancement. The third module "gc3" 705 determines finally the output gain G. Each of these modules is described in more detail below. Here n denotes the time index.

Module "gc1"

The "gc1" module 701 plays a crucial role in the algorithm, since the decision whether the signal component should be enhanced or suppressed is done here. A possible implementation may be, without limitation, as follows: Assume a transient noise is detected, i.e., DTN[n]>0. Then the suppression of the transient noise should start immediately. Thus the "gc1" module sets mod [n]=sup for suppression, and h[n]=max(L,1−$c_{sup}$·DTN[n]), where 0<L<1 is the lower bound for the signal f, and the parameter $c_{sup}$ controls the amount of the indicator DTN[n] to the suppression. During the time interval of the suppression of a transient noise (f<1), all detected transient speech features may be ignored. An additional detected transient noise may increase the suppression again. If the suppression has finished and a transient speech feature is detected (DTS[n]>0), then the enhancement may start by setting mod [n]=enh and h[n]=max(L,1−$c_{enh}$·DTS[n]) with the parameter $c_{enh}$. The parameters $c_{sup}$ and $c_{enh}$ may differ. Exemplary pseudo code for the module "gc1" follows:

■ If [ DTN[n] == 0 & ( f[n − 1] == 1 | mod[n] == enh) ] // if [ no transient noise detected AND ( suppression finished OR enhancement mode is active ]
  ● h[n] = max(L,1 − $c_{enh}$ · DTS[n])
  ● mod[n] = enh
■ Else // a transient noise is detected or the suppression is not finished, i.e., f[n − 1] < 1
  ● h[n] = max(L,1 − $c_{sup}$ · DTN[n])
  ● mod[n] = sup Module "gc2"

The "gc2" module 703 may include parameters $a_{sup}$, $a_{enh}$, $r_{sup}$ and $r_{enh}$ which controls the attack and release time in the suppression and enhancement mode. In each mode the calculation is the same, but the parameter values differ. The calculation may illustratively be done by $$f[n] = \begin{cases} f[n-1] + r_{mod} \cdot (h[n] - f[n-1]) & \text{if } h[n] > f[n-1] \\ h[n] + a_{mod} \cdot (f[n-1] - h[n]) & \text{if } h[n] \leq f[n-1] \end{cases}.$$

For the suppression mode a fast attack ($h[n] \leq f[n-1]$) is desired to reduce the amount of a transient noise immediately, i.e., $a_{sup} \ll 1$. If $h[n] > f[n-1]$, an exponentially increasing gain is applied, where the parameter $r_{sup}$ controls the release time, which should correspond to the duration of the transient noise. For the enhancement mode a slower attack time is desired to smoothly start the enhancement, i.e., $0 \ll a_{enh} < 1$. The release time is again controlled by the parameter $r_{enh}$, which may correspond to the offset time of the respective speech transient.

Module "gc3"

The "gc3" module 705 determines the output gain. Illustratively, the output gain may be, without limitation, calculated by $$G[n] = \begin{cases} f[n] & \text{if } mod[n] = sup \\ q_g + (1 - q_g) \cdot f[n] & \text{if } mod[n] = enh \end{cases}.$$

The parameter $q_g > 1$ defines the maximal enhancement.

Gain Application Module

In the gain application modules M1, . . . , MK 507, the calculated gains are applied to the envelopes, i.e., $y_k = x_k \cdot G_k$.

FIGS. 8(a-d) show envelopes and corresponding gains for various speech transients, in accordance with various embodiments of the invention. More particularly, FIGS. 8(a-b) show envelopes and corresponding gains for various speech transients, in accordance with various embodiments of the invention, in the frequency range from 6811 Hz to 9000 Hz after the filter bank ($s_k$), the stationary noise reduction stage/module ($x_k$), and the transient modification stage/module TMS ($y_k$), respectively. FIG. 8(a) shows the envelopes for a speech transient that includes the consonant [s], while in FIG. 8(b), the corresponding gains are shown, in accordance with an embodiment of the invention. The signal $env_{FB}$ refers to the envelope of the signals $s_k$ output by the filter bank (FB) 401, the signal $env_{NR}$ to the signals $x_k$ output by the noise reduction (NR) module 403 and $env_{TR}$ to the signals $y_k$ output by the transient modification stage (TMS) 405. Up to time 4.36 seconds, the stationary noise reduction erroneously decreases the envelope and blurs the onset of speech, since the detector in the module (NR) 403 identifies speech too slowly. Afterwards, the envelope value is maintained, i.e., the applied gain $gain_{NR}$ of noise reduction (NR) module 403 is equal to 1. In TMS, the consonant is detected earlier. Some parts of the suppression applied by the noise reduction (NR) module 403 are compensated, and parts of the consonant are enhanced. In doing so, the transient modification corrects/counteracts the erroneous (slow) processing. In FIGS. 8(c) and 8(d), the same properties can be found in the low frequencies for the vocal [ø:], in accordance with an embodiment of the invention. Here, the TMS enhances the onset of the vocal. In FIG. 8(c) it can be seen that the onset during the timespan from 3.3 seconds to 3.35 seconds is enhanced. The signal $env_{TR}$ output by the TMS 405 is larger than the signal $env_{NR}$ output by the NR module 403 and the $env_{FB}$ signal. The signal $env_{NR}$ is lower than $env_{FB}$ and showing the unwanted applied suppression by the noise reduction (NR) module 403. The TMS 405 corrects/counteracts this unwanted behaviour of the noise reduction (NR) module 403. In addition it can be seen, that the signal $env_{TR}$ is larger during the onset period as compared to the signal $env_{FB}$ from the filter bank and thereby enhancing the speech signal during the onset period compared to the digitized sound signal s.

FIG. 9(a) shows a possible undesired side effect of this onset enhancement when a noise transient occurs but a transient speech feature is erroneously determined by TMS, in accordance with an embodiment of the invention. In particular, envelopes $env_{FB}$, along with $env_{NR}$, and $env_{TR}$ are shown. Up to time approx. 3.025 seconds, the stationary noise reduction stage/module decreases the onset of the transient noise. But in TMS, the onset is wrongly determined as a transient speech feature up to 3.023 seconds, and thus the transient noise is enhanced. After the transient noise detector identifies the transient noise, the reduction is applied. FIG. 9(b) shows the corresponding gains, in accordance with an embodiment of the invention. In various embodiments, a modification of the gain calculator module 505 may address the unwanted enhancement, in accordance with an embodiment of the invention. If a transient noise is detected, the gain up to a certain time (in this case, without limitation, 20 ms) before the detected transient noise has begun, may be modified. To realize this a delay may advantageously be introduced, preferably the delay is 10 ms. In other embodiments, the delay may be, for example, 15 ms or 20 ms, or any other desired delay. The modified gain within this time (e.g. 20 ms) may be interpolated from the gain value by the delay before (e.g. 20 ms) the transient noise has begun to the gain value at the instant the transient noise is detected. The interpolation may be linear. In another embodiment, the interpolation may be logarithmic or exponential. FIGS. 9(c) and 9(d) show the corresponding envelopes and gains, respectively, in which a linear interpolation of the gain of TMS is applied between the gain value 20 ms before and at location of the detection of the transient noise. Additionally or alternatively, the calculated gains in TMS may be low-pass filtered. Hereinafter, this above-described modification to the gain will be referred to as TMSs and the gain and envelope signals as $gain_{TRs}$ and $env_{TRs}$, respectively. The whole transient noise can thus be suppressed, but, as described above, an additional delay (e.g., 20 ms) is introduced. It should be noted, that the additional delay is short enough and does not introduce any unwanted side-effects on e.g. speech percept or sound source localization.

Spectrograms of the signal-changes of the TMS are shown in FIG. 10(a), and of the TMSs in FIG. 10(b), in accordance with various embodiments of the invention. In both FIGS. 10(a) and 10(b), the enhancements of the consonants and of the onsets of vocals are visible. In FIG. 10(a), the onset of the transient noise is also enhanced, while the modification of the gain prevents that in FIG. 10(b). Furthermore, the influence of the low pass filter on the gains can be seen by the smoother enhancement in the bottom spectrogram. Note that in FIGS. 10(a) and 10(b), the suppression of transient noise is restricted to frequencies greater than approximately 1450 Hz. Furthermore, the delay of 20 ms in FIG. 10(b) is ignored for an easier comparison.

FIG. 11(a) shows the resulting gain within the frequency range of 5034.5-6811 Hz corresponding to the input sound signal s, in accordance with an embodiment of the invention. FIG. 11(b) shows the resulting gain within the frequency range of 6811-9000 Hz corresponding to the input sound signal s, in accordance with an embodiment of the invention. Here, the attenuation of the two transient noise signals and the enhancement of the speech transients is visible. Note that the suppression is applied to both frequency regions, whereas the enhancement of transient speech is restricted to frequencies where the speech feature occurs. The enhancement of onsets of speech features can also be seen. The time delay of 20 ms is again ignored for an easier comparison with the other plots.

FIG. 12(a) shows a spectrogram associated with input signal s after the filter bank, in accordance with an embodiment of the invention. FIG. 12(b) shows a spectrogram associated with the input signal s after the stationary noise reduction, in accordance with an embodiment of the invention. FIG. 12(c) shows a spectrogram associated with the input signal s after transient modification, in accordance with an embodiment of the invention. The suppression and the enhancement of transient noise and speech are clearly visible.

In various embodiments, the envelopes after the TMS module may be restricted to the value of the envelopes after the filter bank to reduce distortion due to a too large enhancement. The internal signals of the stationary noise reduction may be included in the TMS processing. Exemplary signals may include the output of a voice activity detector detecting speech absent and speech present periods or the estimated signal-to-noise ratio. The application of the calculated gain in the TMS module may be different, for example an N-of-M coding strategy could be controlled by the gain, thus leading to a modified channel selection and stimulation. Instead of the calculated gain, coefficients of an FIR filter may be calculated, which are applied to the envelopes.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of generating electrode stimulation signals for electrode contacts in an electrode array associated with a hearing implant, the method comprising:
   processing an input audio signal to generate a plurality of band pass channel signals each representing an associated band of audio frequencies;
   applying stationary noise reduction so as to provide a stationary noise reduced channel envelope from each channel signal;
   detecting a transient in one or more of the channel envelopes;
   modifying the channel envelopes as a function of whether the transient is transient noise or transient speech, so as to form transient modified envelopes; and
   using the transient modified envelopes to generate electrode stimulation signals to the electrode contacts.

2. The method according to claim 1, wherein
   if the transient is transient noise, reducing the transient noise in one or more of the channel envelopes to form the transient modified envelopes; and
   if the transient is transient speech, enhancing the transient speech in one or more of the channel envelopes to form the transient modified envelopes.

3. The method according to claim 1, wherein detecting the transient includes:
   determining for each channel envelope a channel-specific transient noise indicator characterizing transient noise present in the channel signal; and
   determining for each channel envelope a channel-specific transient speech indicator characterizing transient speech present in the channel signal.

4. The method according to claim 3, wherein the channel-specific transient noise indicator is based on a proportion of power of the channel envelope to power of the input audio signal.

5. The method according to claim 3, wherein determining the channel-specific transient noise indicator includes high-pass filtering the channel envelope.

6. The method according to claim 3, wherein determining for each channel envelope a channel-specific transient speech indicator is includes:
   high-pass filtering the channel envelope;
   low-pass filtering the channel envelope;
   determining ranges of the high-pass filtered channel envelope, the low-pass filtered channel envelope, and the channel envelope; and
   determining for each channel envelope a channel-specific transient speech indicator as a function of the determined ranges.

7. The method according to claim 3, wherein modifying the channel envelopes includes:
   applying a channel-specific gain to each channel envelope as a function of their associated transient noise indicator and transient speech indicator to produce the transient modified envelopes.

8. The method according to claim 7, further comprising introducing a time delay that, upon detection of transient noise, allows modification of the applied channel-specific gain up to a predetermined time prior to the detected transient noise.

9. The method according to claim 7, wherein modifying the channel envelopes includes limiting amplitude of the channel envelopes to reduce distortion resulting from a large enhancement.

10. The method according to claim 1, wherein the hearing implant is one of a totally implantable cochlear implant, a cochlear implant having both an external speech processor and an implanted stimulator that includes the electrode array, and an auditory brainstem implant.

11. A signal processing arrangement for generating electrode stimulation signals for electrode contacts of an electrode array associated with a hearing implant, the arrangement comprising:
   a filter bank pre-processor configured to process an input audio signal to generate a plurality of band pass channel signals each representing an associated band of audio frequencies;
   a stationary noise reduction (NR) module configured to reduce stationary noise in each channel and provide a stationary noise reduced channel envelope from each channel signal;
   a transient modification stage (TMS) configured to:
      detect a transient in one or more of the channel envelopes; and
      modify the channel envelopes as a function of whether the transient is transient noise or transient speech, so as to form transient modified envelopes; and
   a stimulation signal generator configured to use the transient modified envelopes to generate electrode stimulation signals to the electrode contacts.

12. The arrangement according to claim 11, wherein the transient modification stage is configured to:
   if the transient is transient noise, reduce the transient noise in one or more of the channel envelopes to form the transient modified envelopes; and
   if the transient is transient speech, enhance the transient speech in one or more of the channel envelopes to form the transient modified envelopes.

13. The arrangement according to claim 12, wherein the transient modification stage determines for each channel envelope a channel-specific transient noise indicator characterizing transient noise present in the channel signal, and determines for each channel envelope a channel-specific transient speech indicator characterizing transient speech present in the channel signal.

14. The arrangement according to claim 13, wherein the transient modification state determines the channel-specific transient noise indicator based on a proportion of power of the channel envelope to power of the input audio signal.

15. The arrangement according to claim 13, wherein the transient modification state determines the channel-specific transient noise indicator based on high-pass filtering the channel envelope.

16. The arrangement according to claim 13, wherein the transient modification stage includes:
   a high-pass filter for filtering the channel envelope; and
   a low-pass filter for filtering the channel envelope,
   wherein the transient modification stage is further configured to determine ranges of the high-pass filtered channel envelope, the low-pass filtered channel envelope, and the channel envelope, and determine for each channel envelope a channel-specific transient speech indicator as a function of the determined ranges.

17. The arrangement according to claim 13, wherein the transient modification stage is further configured to apply a channel-specific gain to each channel envelope as a function of their associated transient noise indicator and transient speech indicator to produce the transient modified envelopes.

18. The arrangement according to claim 17, wherein the transient modification stage is configured to provide a time delay that, upon detection of transient noise, allows modification of the applied channel-specific gain up to a predetermined time prior to the detected transient noise.

19. The arrangement according to claim 17, wherein the transient modification stage is configured, when modifying the channel envelopes, to limit amplitude of the channel envelopes to reduce distortion resulting from a large enhancement.

20. The arrangement according to claim 11 wherein the hearing implant is one of a totally implantable cochlear implant, a cochlear implant having both an external speech processor and an implanted stimulator that includes the electrode array, and an auditory brainstem implant.

* * * * *

UNITED STATES PATENT AND TRADEMARK OFFICE
CERTIFICATE OF CORRECTION

PATENT NO. : 9,498,626 B2
APPLICATION NO. : 14/564818
DATED : November 22, 2016
INVENTOR(S) : Florian Frühauf et al.

Page 1 of 1

It is certified that error appears in the above-identified patent and that said Letters Patent is hereby corrected as shown below:

In the Claims

In Column 17, Line 6:
Delete "is"

Signed and Sealed this
Thirteenth Day of February, 2018

Andrei Iancu
*Director of the United States Patent and Trademark Office*